(12) United States Patent
Borzatta et al.

(10) Patent No.: US 8,025,894 B2
(45) Date of Patent: Sep. 27, 2011

(54) INNOVATIVE FORMULATION

(75) Inventors: Valerio Borzatta, Bologna (IT); Oreste Picolo, Sirtori (IT); Elisa Capparella, Ravenna (IT)

(73) Assignee: Endura S.p.A., Bologna (IT)

( * ) Notice: Subject to any disclaimer, the term of this patent is extended or adjusted under 35 U.S.C. 154(b) by 858 days.

(21) Appl. No.: 11/912,299

(22) PCT Filed: Apr. 20, 2006

(86) PCT No.: PCT/EP2006/061688
§ 371 (c)(1),
(2), (4) Date: Oct. 22, 2007

(87) PCT Pub. No.: WO2006/111553
PCT Pub. Date: Oct. 26, 2006

(65) Prior Publication Data
US 2009/0130156 A1 May 21, 2009

(30) Foreign Application Priority Data
Apr. 22, 2005 (IT) .............. MI2005A0728

(51) Int. Cl.
*A01N 25/28* (2006.01)

(52) U.S. Cl. ........ 424/408; 424/405; 424/406; 424/417; 424/419

(58) Field of Classification Search .......... None
See application file for complete search history.

(56) References Cited

U.S. PATENT DOCUMENTS

| | | | |
|---|---|---|---|
| 4,056,610 A * | 11/1977 | Barber et al. ............... | 424/419 |
| 4,524,068 A | 6/1985 | Szejtli et al. | |
| 4,936,901 A * | 6/1990 | Surgant et al. ............ | 504/133 |
| 5,707,638 A | 1/1998 | Losel et al. | |

FOREIGN PATENT DOCUMENTS

| | | |
|---|---|---|
| DE | 24 11 373 A1 | 9/1975 |
| DE | 37 08 671 A1 | 9/1987 |
| EP | 0 282 706 A | 9/1988 |
| GB | 1 513 614 A | 6/1978 |
| WO | WO 97/14308 A | 4/1997 |

(Continued)

OTHER PUBLICATIONS

Benchaoui, H.A. And McKellar, Q.A. 1996 "Interaction between Fenbendazole and Piperonyl Butoxide: Pharmacokinetic and Pharmacodynamic Implications" *J Pham Pharmacol* 48:753-759.

(Continued)

*Primary Examiner* — Neil Levy
(74) *Attorney, Agent, or Firm* — Knobbe Martens Olson & Bear LLP (57) ABSTRACT

The present invention relates to a new formulation characterised by the presence of two components, one of which (A) possesses insecticidal, acaricidal, fungicidal, snailcidal or vermicidal activity and the other (B) exhibits synergistic activity with the first by enhancing its effectiveness, and in which the average release time of component (A) is 1 to 12 hours later than the average release time of component (B). The formulation is obtained by: a) separate microencapsulation of both components (A) and (B) within a multilayer system of specific polymers in which component (A) is in a more interior portion of the capsule than component (B), being separated from component (B) by a polymer layer of suitable thickness (FIG. 1); b) microencapsulation of both components within a single layer system (FIG. 2), combined with an immediate-release emulsion/microemulsion containing an additional amount of component (B).

20 Claims, 1 Drawing Sheet

FOREIGN PATENT DOCUMENTS

| | | |
|---|---|---|
| WO | WO 03/092378 A | 11/2003 |
| WO | WO 2005/039287 A2 | 5/2005 |

OTHER PUBLICATIONS

Finch, C.A. 1993 "Industrial Microencapsulation: Polymers for Microcapsule Walls" *Special Publication Rolay Soc Chem* 138:1-12.

Gimeno, M. 1996 "An Overview of the Latest Development of Microencapsulation for Agricultural Products" *J. Environ. Sci. Health*, B31(3):407-420.

Gunning, R.V. et al. 1998 in *Piperonyl Butoxide*, Chapter 13, "Inhibition of Resistance-related Esterases by Piperonyl Butoxide in *Helicoverpa atmigera* (Lepidoptera: Noctuidae) and *Aphis gossypii* (Hemiptera: Aphididae)" *Academic Press* pp. 215-226.

Nishiwaki, H. et al. 2004 "Metabolism of Imidacloprid in Houseflies" *J Pestic Sci* 29:110-116.

Wen, Z. and Scott, J.G. 1997 "Cross-Resistance to Imidacloprid in Strains of German Cockroach (*Blattella germanica*) and House Fly (*Musca domestica*)" *Pestic Sci* 49:367-371.

Zhao, J.-Z. et al. 2000 Inheritance and Synergism of Resistance to Imidacloprid in the Colorado Potato Beetle (Coleoptera: Chrysomelidae) *J Econ Entomology* 93:1508-1514.

Gunning R.V. et al. (1999) Esterase inhibitors synergise the toxicity of pyrethroids in Australian *Helicoverpa armigera* (Hubner) (Lepidotera: Noctuidae) Pesticide Biochemistry ad Physiology 63:50-62.

Database WPI Section Ch, Week 199003 Derwent Publications Ltd., London, GB; An 1990-019276 XP002322687 & JP 01 299203 A, Dec. 4, 1989.

Biebel, R. et al. (2003) "Action of pyrethrum-based formulations against weevils" International Journal of Pharmaceutics 256:175-181.

Lajos, S. et al. (1990) "Formulation of insect controlling agents with B-cyclodextrin" Pesticide Science, Elsevier Applied Science Publisher. Barking, GB, 28:7-16.

\* cited by examiner

INNOVATIVE FORMULATION

This application is the U.S. National Phase under 35 U.S.C. §371 of International Application PCT/EP2006/061688, filed Apr. 20, 2006, which claims priority to Italian Patent Application No. MI2005A000728, filed Apr. 22, 2005.

FIELD OF THE INVENTION

The present invention relates to the field of insecticide, acaricide, fungicide, snailcide and vermicide compositions, particularly those in which the active principle (A) is mixed with synergistic substances (B) having various mechanisms of action, for example substances inhibitory to detoxification mechanisms in insects. New formulations in microcapsules based on polyesters, polyamides, polyureas, polycarbamates, polyurethanes or urea-formaldehyde polymers are described in which the effect of (A) and (B) is further enhanced by the different release times of the two components, and in which the average release time of component (A) $[t_{(A)}]$ is delayed by a time interval $\Delta t=[t_{(A)}]-[t_{(B)}]$ of between 1 and 12 hours, preferably between 2 and 10 hours, relative to the average release time of component (B) $[t_{(B)}]$. Said innovative formulations are particularly more effective than those available commercially, mainly against damaging species which have developed resistance to the biological activity of component (A).

PRIOR ART

The problem of tolerance and resistance to insecticidal, acaricidal, fungicidal, snailcidal and vermicidal activity is particularly serious and of growing importance, leading to the ever more difficult control and eradication of damaging species (insects, mites, moulds, snails, worms) so that protection against their action in agriculture, veterinary medicine, domestic hygiene and in manufactured articles becomes necessary.

Many damaging species have strengthened their natural defenses and immune systems against the toxins with which they come into contact, so that to achieve their eradication, dosages have to be increased or new insecticides, acaricides, fungicides, snailcides or vermicides must be continually used with consequent greater risks and damage to the entire ecosystem and the overall food chain up to man, and with rising costs.

It is widely reported in the literature that the use of substances such as piperonyl butoxide (PBO) and its analogues, sesamol, verbutin, MGK 264 and DEF, can enhance insecticidal, acaricidal, fungicidal, snailcidal and vermicidal activity in vitro and/or in vivo, either by inhibiting the activity of certain insect metabolic enzymes involved in detoxification and resistance or by other mechanisms of action [see for example Gunning R. V. et al., "Piperonyl Butoxide", pages 215-225, Academic Press (1998); Benchaoui H. A. et al. J. Pharm. Pharmacol. 1996, 48, 753-759; Wen Z. et al., Pest. Science 1997, 49, 367-371; Zhao J-Z J. Econ. Entomol. 2000, 93, 1508-1514; Nishiwaki H. et al., J. Pest. Science 2004, 29, 110-116 and the patent applications DE 4426942, EP 617890].

In order to better demonstrate the synergistic activities, particularly in cases where the damaging species is most resistant, treatment with the synergistic product at different times prior to the active principle or a repeated treatment with active principle was proposed; pre-treatment with the synergistic compound is particularly beneficial in that subsequent exposure to the active principle occurs on the already sensitised damaging species, thus with weakened capacity to defend themselves, and is therefore more effective. Separate administrations however are not very practical and are economically unfavourable compared with a single application of the two components.

Also described in the literature and in patent applications are insecticide, acaricide, fungicide, snailcide and vermicide formulations in microcapsules based on polymers such as polyesters, polyamides, polyureas, polycarbamates, polyurethanes or based on urea-formaldehyde polymers, and the corresponding preparation procedures [see for example Gimeno M., J. Environ. Sci. Health, 1996, B31(3), 407-420, Finch C. A. in "Encapsulation and controlled release", special publication, Royal Society of Chemistry 1993, 138, 1-12 and the patent applications EP183999, WO03/051116, US2003/0119675, US2002/0158356 A1, WO00/04776, EP 322820]. The main purposes of said formulations are: greater stability, prolonged biological effect due to a gradual release over time with consequent dilution of side-effects over time, and lower toxicity for operators, other animal species and the ecosystem etc. Although some principles and the methodology of this type of formulation have been known for some time, in order to follow the established objectives it is nevertheless necessary to modulate the characteristics of the encapsulation system.

The use of some active principles microencapsulated in polymer matrices based on polyesters, polyamides, polyureas, polycarbamates, polyurethanes or based on urea-formaldehyde polymers in optional combination with non-encapsulated or separately encapsulated synergistic products has been generically described [ZA 8700881, DE3708671] while a formulation simultaneously containing an insecticide active principle (A) and a synergistic compound (B) in a monolayer or multilayer microcapsule is exemplified and claimed in WO97/14308, without however any data on improvement of biological activity compared to the same microencapsulated product in the absence of the synergistic compound. The previous literature, even when combined, has therefore not provided the expert of the art with any useful information for preparing the innovative formulation of the present invention, nor has it suggested an effectiveness of said formulation surprisingly superior to that of a mixture of the two components (A) and (B) administered simultaneously on insecticidal, acaricidal, fungicidal, snailcidal or vermicidal activity for agricultural applications, for veterinary medicine use, for domestic hygiene or for the protection of manufactured articles. The result achieved with the present invention enables to overcome the drawbacks of the known art and to significantly improve the performance of commercially known active principles by means of a single treatment, particularly for resistant damaging species.

SUMMARY OF THE INVENTION

The present invention relates to an innovative formulation, characterised by the presence of two components, one of which (A) possesses insecticidal, acaricidal, fungicidal, snailcidal or vermicidal activity and the other (B) exhibits synergistic activity with the first by enhancing its effectiveness, and in which the average release time of component (A) $[t_{(A)}]$ is delayed by a time interval $\Delta t=[t_{(A)}]-[t_{(B)}]$ of between 1 and 12 hours, preferably between 2 and 10 hours, relative to the average release time of component (B) $[t_{(B)}]$.

The invention also relates to its use for eradicating damaging species in agriculture, veterinary medicine, domestic hygiene or in manufactured articles.

Figure 1:
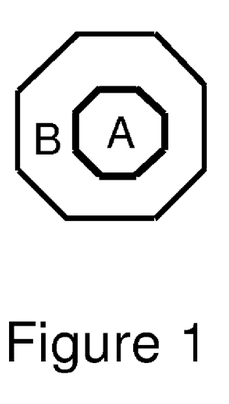
FIG. 1 shows individual microencapsulation of both components (A) and (B) within a multilayer system.
Figure 2:
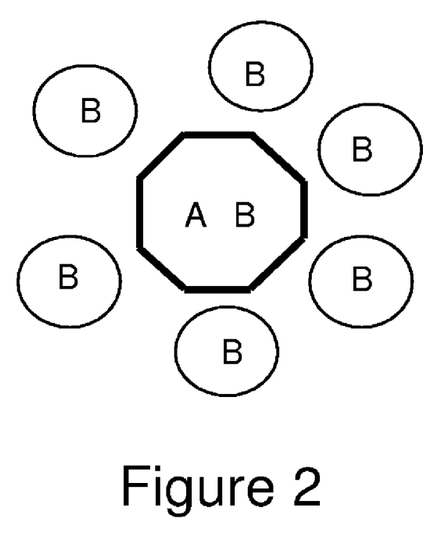
FIG. 2 shows microencapsulation of both components within a single layer system of suitable thickness in combination with an immediate-release emulsion/microemulsion containing an additional amount of component (B).

The new formulation is obtained according to one of the following alternatives using per se known procedures (in addition to the scientific and patent literature already cited, see for example the following U.S. Pat. No. 3,577,515, U.S. Pat. No. 4,280,833, U.S. Pat. No. 4,285,720 and patent application US 2002/0158356 whose teachings are herein incorporated).

a) individual microencapsulation of both components (A) and (B) within a multilayer system based on polyesters, polyamides, polyureas, polycarbamates, polyurethanes or urea-formaldehyde polymers in which component (A) is in a more interior portion of the capsule than component (B), and is separated from the latter by a polymer layer of suitable thickness as in FIG. 1;

b) microencapsulation of both components within a single layer system of suitable thickness based on polyesters, polyamides, polyureas, polycarbamates, polyurethanes or urea-formaldehyde polymers as in FIG. 2, in combination with an immediate-release emulsion/microemulsion containing an additional amount of component (B).

When the polymer is polyurea, the process is as follows:
a) an oil phase, containing the component (A) alone or (A)+(B) to be encapsulated, a possible solvent (e.g. Solvesso 200) if the active substances are solids, and a polyisocyanate alone or mixed with a variable quantity of a different polyisocyanate e.g. toluene diisocyanate, is dispersed in an aqueous phase containing a surfactant such as a lignin sulfonate
b) a polyamine such as hexamethylenediamine which gives rise to polymerisation is then added, or alternatively heating is applied to induce a partial hydrolysis of the isocyanate groups which subsequently self-condense under hot conditions
c) the capsules thus formed consist of a polyurea wall within which component (A) alone or components (A)+(B) are present
d) where the capsule contains component (A) alone, the operation can be repeated such that the new polymerisation takes place this time in the presence of the species (B) to obtain multilayer capsules such as those shown in FIG. 1.

Alternatively if the single layer capsule already contains the two components (A) and B, a emulsion/microemulsion formed by mixtures of anionic and nonionic surfactants containing the immediate-release component (B) is added in order to obtain the desired formulation (FIG. 2).

In general the material constituting the capsule wall represents a fraction of the capsule weight, ranging between 5% and 30%.

When the polymer is polyamide the process is as follows:
a) an oil phase, containing the component (A) alone or (A)+(B) to be encapsulated, a possible solvent (e.g. Solvesso 200) if the active substances are solids, and an acid chloride e.g. sebacoyl chloride alone or mixed with a variable quantity of other acid chlorides, is dispersed in an aqueous phase containing a surfactant such as a lignin sulfonate
b) a polyamine or a polyoxyalkylene polyamine (e.g. Jeffamine D-230) is added, alone or mixed with ammonia or with other amines or inorganic bases neutralizing the acidity formed during polymerisation
c) the capsules thus formed consist of a polyamide wall, formed by discontinuous or continuous process, within which component (A) alone or components (A)+(B) are present.
d) where the capsule contains component (A) alone the operation can be repeated so that the new polymerisation takes place this time in the presence of the species (B) to obtain multilayer capsules such as those shown in FIG. 1.

Alternatively if the single layer capsule already contains the two components (A) and B, a emulsion/microemulsion formed by mixtures of anionic and nonionic surfactants containing the immediate-release component (B) is added in order to obtain the desired formulation (FIG. 2).

In a similar manner, capsules can be formed having as membrane a polyester, a polycarbamate, a polyurethane or a urea-formaldehyde polymer by selecting suitable monomer precursors of the capsule polymer.

By adjusting the relative ratio of the quantities of co-monomers as well as the relative ratio of the quantities of substances to be encapsulated and the quantities of components of the polymer and the surfactant, the thickness and structure of the capsule membrane can be controlled. Other modulatable parameters for this purpose are: temperature and time of polymerisation, quantity of solvent, use of polymerisation inhibitors in suitable quantities, addition of polymer cross-linking substances. Consequently the time of encapsulated substance release can be controlled as can, most important for the purposes of the present invention, the average release time of component (A) $[t_{(A)}]$ being delayed by a time interval $\Delta t = [t_{(A)}] - [t_{(B)}]$ of between 1 and 12 hours, preferably between 2 and 10 hours, relative to the average release time of component (B) $[t_{(B)}]$.

By "average release time $[t_{(A)}]$" it is meant the time by which 50% (by weight) of the total amount of (A) present in the microcapsule has been released.

By "average release time $[t_{(B)}]$", it is meant the time by which 50% (by weight) of the total amount of (B) present in the microcapsule has been released; in the particular embodiment of FIG. 2, $[t_{(B)}]$ is always set to zero because the immediate-release emulsion/microemulsion releases (B) immediately after administration; the immediate-release emulsion/microemulsion always contains 50% or more of the total (B) present in the formulation, therefore $[t_{(B)}]$ in FIG. 2 cannot be higher than zero; accordingly, in FIG. 2, $[t_{(B)}]=0$, and $\Delta t = [t_{(A)}]$.

The term "immediate-release" is used to highlight the standard behaviour of emulsions/microemulsions, which do not cause any appreciable delay in releasing the emulsified active principle, as compared to normal solutions; thus no particular provisions are required for preparing the immediate-release emulsions/microemulsions of component (B), and they can be obtained by reference to standard procedures for preparing emulsions/microemulsion.

The microcapsules of the invention are stable when moist; the breakage of the microcapsule wall and, consequently, the phenomenon of release initiates immediately when microcapsules start to dry.

As stated above, the release from the microcapsules initiates immediately after the solution is removed, i.e. typically when the formulation is applied/sprayed e.g. onto a plant, in the ground, in the air, etc). In this way, the above referred $\Delta t$ corresponds to the actual difference in time of administration to plants and insects.

The determination of $t_{(A)}$ and $t_{(B)}$) can be made as follows. An aliquot of the suspension of the microcapsules is immediately put onto a series of glass plates; the loaded glass plates are maintained at standard ambient conditions for different times; at the end of each time, the corresponding glass plate is washed with a solvent of (A) or (B) which is not solvent of the microcapsule wall (typically n-hexane); in such a way only the released components are extracted for quantification, by e.g. HPLC. The time corresponding to a 50% release (as compared to the total (A) or (B) loaded into the microcapsules), will be respectively the $t_{(A)}$ or $t_{(B)}$.

Other well known techniques such as electron microscopy enable to determine the average diameter of the microcapsules, being in the range of 1-100 micron, preferably less than 50 micron.

The new formulation is particularly effective against damaging species that have developed resistance to treatment with the same active substance, and induces, for the same quantity of active principle, a substantially higher mortality of the damaging species than that demonstrated by the same components (A) and (B) used in a mixture as such or microencapsulated separately within the same polymer materials or microencapsulated jointly but with the same release time.

DETAILED DESCRIPTION OF THE INVENTION

The polymers constituting the microcapsules can be polyesters, polyamides, polyureas, polycarbamates, polyurethanes or based on urea-formaldehyde polymers. Polymerisation is performed in accordance with methods known to the expert of the art.

Active principles (A) usable in the present invention belong to one of the following classes of chemical products: pyrethroids, carbamates, organophosphates, thioureas, pentatomic or hexatomic heterocycles where 1, 2 or 3 nitrogen atoms are present, such as pyridine, pyrrole, imidazole, benzimidazole, thiazole, pyrazole, pyridazine, quinazoline, oxadiazine, triazine. Particularly preferred are: 1) pyrethroids such as Allethrin, Bioallethrin, Tetramethrin, Prallethrin, Cypermethrin, α-Cypermethrin, β-Cypermethrin, ξ-Cypermethrin, Esbiothrin, Permethrin, Fenpropathrin, Transfluthrin, Bifenthrin, Resmethrin, Bioresmethrin, Fenvalerate, Esfenvalerate, Tetramethrin, Imiprothrin, Phenothrin, β-Cyfluthrin, Deltamethrin, Cyhalothrins, Etofenprox, Silafluofen, extracts of pyrethrum and mixtures thereof etc., 2) neonicotinoids such as Imidacloprid, Acetamiprid, Thiacloprid, Thiamethoxam and AKD1022; 3) carbamates such as Pirimicarb, Aldicarb, Thiodicarb, Carbosulfan, Carbofuran and Propoxur; 4) organophosphates such as Profenofos, Dimethoate, Omethoate, Terbufos, Azinphos-methyl, Pirimiphos-methyl, Demeton-s-methyl, Fenitrothion, Trichlorfon and Malathion; 5) mitochondrial electron transport inhibitors ("METI") such as Fenazaquin, Tebufenpyrad, Fenpyroximate, Pyridaben and Tolfenpyrad; 6) fungicides such as Fludioxonil, Clotrimazole, Imazalil and Pyrimethanil; 7) vermicides such as Mebendazole, Metronidazole, Fenbendazole, Thiabendazole, Clotrimazole and Praziquantel; 8) nerve transmission inhibitors such as Indoxacarb and Fipronil; 9) other active principles such as Pymetrozine, Chlorfenapyr and Pyridalyl.

Within the above classes of compounds, even more preferred are: Allethrin, Bioallethrin, Tetramethrin, Prallethrin, Cypermethrins, Esbiothrin, Permethrin, Fenpropathrin, Transfluthrin, Bifenthrin, Resmethrin, Bioresmethrin, Fenvalerate, Esfenvalerate, Etofenprox, Imiprothrin, Phenothrin, β-Cyfluthrin, Deltamethrin, λ-Cyhalothrin, Imidacloprid, Acetamiprid, Thiacloprid, Thiodicarb, Carbosulfan, Carbofuran, Fenazaquin, Pyridaben, Fludioxonil, Imazalil, Pyrimethanil, Fenbendazole, Clotrimazole, Praziquantel, Fipronil, Pymetrozine and Pyridalyl.

The quantities of monomers (i.e. the components of the encapsulating polymer) relative to the material to be encapsulated are preferably between 1% and 50% (weight/weight) and even more preferably between 2% and 30%.

Components able to synergistically enhance the activity of active principle (A) are substances known and already in use. Preferred examples of synergistic compounds (B) are piperonyl butoxide (PBO) and its analogues, sesamol, verbutin, MGK 264 and DEF, with PBO and its analogues and verbutin being preferred. PBO is particularly preferred. The synergistic compounds can be used as such or already pre-formulated with additives; an example of a commercially available pre-formulation is designated as PB80EC-NF which contains 88% PBO and 12% emulsifier (dialkylsulfosuccinate, also known as SOITEM).

The quantity of component (A) relative to component B (calculated in its total quantity, i.e. both that co-encapsulated with (A) and that present in the emulsion/microemulsion), is between 1% and 1500%, preferably between 2% and 200% and even more preferably between 5% and 100%.

Emulsifiers, UV stabilizers, antioxidants and other additives non-specific for active principle activity but useful for the specific application can also be present in the aforesaid formulation.

The quantity of said additives relative to the constituent polymer of the capsule is preferably between 0% and 30% (weight/weight), more preferably between 1% and 15%. These percentages refer to all additives present, also including those already present in the pre-formulations of the active principles utilized.

Usable emulsifiers are for example dodecylbenzenesulfonate, dialkylsulfosuccinate, lignin sulfonates, phospholipids, polyethylene glycols.

Usable UV stabilizers are for example 2-hydroxy-4-methoxy-benzophenone, 2-hydroxy-4-octoxy-benzophenone, 4-hydroxy-2,2,6,6-tetramethylpiperidine sebaca-te. A usable antioxidant is for example 2,6-di-tert-butyl-1-hydroxy-toluene.

For those formulations of the present invention wherein a synergistic compound is also present as a emulsion/microemulsion, the latter can be the same as or different from that present in the microcapsule.

The composition of the invention can be provided as a solid, as an oily solid/suspension composition or as a homogeneous emulsion/microemulsion and is soluble or completely emulsifiable in water or in aqueous mixtures of water-miscible solvents. Said formulations can be used as such or previously emulsified in water or in aqueous solutions of water-miscible solvents, such as a C1-4 alcohol; the content of water miscible solvent is between 0% and 99%, preferably between 0% and 60%. The process for preparing the microcapsules, forming the basis of the aforesaid compositions, uses per se known technologies.

More specifically the process for preparing the microcapsules can be performed in accordance with one of the following methods, indicated as process (i) and process (ii) respectively.

Process (i) (Multilayer Microcapsule) (FIG. 1):

a) a concentrated aqueous microcapsule suspension containing component (A) is prepared by interfacial polymerisation in a water/oil mixture in the presence of the required quantity of component A, the surfactant and the necessary quantities of suitable monomers and co-monomers of the encapsulating polymer;

b) component (B) and further quantities of the surfactant and suitable monomers and co-monomers of the encapsulating polymer are added to the concentrated aqueous microcapsule suspension obtained in (a), the latter being subjected to further encapsulation.

c) the microcapsules obtained in (b) can be recovered and stored in water or in any other suitable solvent which does not dissolve the microcapsule wall, or in an emulsion/microemulsion containing further amounts of component B.

Process (ii) (Single Layer Microcapsule) (FIG. 2):

a) a concentrated aqueous suspension of microcapsules containing components (A) and (B) is prepared by interfacial polymerisation in a water/oil mixture in the presence of the required quantities of components (A) and B, the surfactant and the necessary quantities of suitable monomers and co-monomers of the encapsulating polymer b) the emulsioned/microemulsioned component (B) (in such a quantity that at least 50% of the total (B) present in the final formulation is contained in the emulsion/microemulsion) and other additives useful for the specific application are added to the concentrated aqueous suspension of microcapsules obtained in (a), to obtain the formulative composition of FIG. 2, ready for use.

The presence of encapsulated component (B) can have various functions useful for the application: for example modulating even more precisely the release time of component A, for the same encapsulating membrane; sensitising damaging species which may have resisted initial contact with component B; possibility of using two different synergists when considered necessary.

Possible further components of said formulations, as previously indicated, can be mixed as solids or as emulsion/microemulsions immediately prior to use.

A further aspect of the invention is the use of said formulations as insecticides, acaricides, fungicides, snailcides or vermicides in agriculture, for veterinary medicine use, for eradicating household insects and for the protection of manufactured articles. The formation of a formulation, characterised by the presence of two components, one of which (A) possesses insecticidal, acaricidal, fungicidal, snailcidal or vermicidal activity and the other (B) exhibits synergistic activity with the first by enhancing its effectiveness, and in which the average release time of component (A) $[t_{(A)}]$ is delayed by a time interval $\Delta t = [t_{(A)}] - [t_{(B)}]$ of between 1 and 12 hours, preferably between 2 and 10 hours, relative to the average release time of component (B) $[t_{(B)}]$, has surprisingly resulted in a significant increase in composition effectiveness compared to mixtures of the two components used as such or microencapsulated individually or microencapsulated jointly but with the same release time. By means of the invention an enhanced interaction between the active principle and the synergistic compound is achieved; in comparative trials performed by the inventors, said enhancement was always found to be greater than 50%; the effect is therefore of great importance.

Enhancement of activity leads to various advantages of industrial significance: for example for the same active substance used, compositions with higher activity can be obtained; or compositions with an effectiveness equal to known compositions can be obtained but with reduced active substance use; the lesser amount of active substance used leads to lowed product cost, lower environmental impact of the manufacturing process, and lower volume/weight ratio of the final composition, with further practical advantages for the operator concerned with the procedures for using these formulations.

Consequently with the present invention insecticide, acaricide, fungicide, snailcide or vermicide formulations are unexpectedly obtained which are highly effective and less costly than known formulations.

The following examples illustrate the invention without however in any way limiting it.

EXPERIMENTAL PART

Example 1

Preparation of a Formulation Based on Bifenthrin+PBO Microencapsulated in Polyurea (PU) and Microemulsified PBO The process for preparing a formulation consisting of an aqueous suspension bifenthrin+PBO microencapsulated (2%) in PU and an o/w 10% PBO emulsion of is described.

a) Premix A (Concentrated Microcapsule Suspension)

Reagents:

| | |
|---|---|
| Pure bifenthrin | 20% |
| PBO | 0.2% |
| Solvent (Solvesso 200) | 20% |
| Voronate M220 | 2.87% |
| Hexamethylenediamine (40%) | 2.75% |
| Lignin sulfonate | 1% |
| Soluble salts of Ca and Na | 9% |
| Silicon antifoam agent | 0.2% |
| Xanthan gum | 0.1% |
| Water | remainder to 100% |

The organic phase, containing the active principles to be encapsulated and the polyisocyanate is dispersed, rapidly and under vigorous stirring, in the aqueous phase containing lignin sulfonate at the temperature of 50° C. Upon reaching phase dispersion, stirring is decreased and hexamethylenediamine is rapidly added. Polymerisation starts rapidly with moderate hexothermy. The mixture is maintained under stirring for 4 hours at 50° C. and then cooled at room temperature and added with silicon antifoam agent, xanthan gum, and soluble calcium and sodium salts, to provide a concentrated microcapsule suspension with a viscosity of 500-1000 cps.

b) Premix B

| | |
|---|---|
| PBO tech (95%) | 81% |
| Emulsifier (mixture of anionic and nonionic surfactants) | 19% |

PBO, technical is mixed with a suitable emulsifying agent consisting of a mixture of anionic and non ionic surfactants.

c) Final Formulation

Reagents:

| | |
|---|---|
| Premix A | 10% |
| Premix B | 13.1% |
| Nonionic polymeric dispersant | 2% |
| Antimould agent | 0.1% |
| Silicon antifoam agent | 0.2% |
| Xanthan gum | 0.15% |
| Water | remainder to 100% |

Premix A and the other components are introduced into a reactor. Premix B is added lastly under sufficient agitation to form a fine emulsion. The formulation thus prepared had the following characteristics:

bifenthrin titre 2%; PBO titre 10%; density 1.01; pH 8-9; viscosity 200-800 cps; microcapsule dimensions (average diameter) 3-10 micron; emulsion size 1-5 micron.

Example 2

Preparation of a Formulation Based on A-Cypermethrin+PBO Microencapsulated in Polyurea (PU) and Microemulsified PBO Using the same method as described in example 1, a formulation is prepared consisting of a PBO emulsion (18%) and an aqueous suspension of a-cypermethrin+PBO encapsulated together (components at 8%) in PU, starting from a premix A containing a-cypermethrin (15%) and PBO (15%) and from a premix B containing PBO (81%), with the following final composition:

| | |
|---|---|
| Premix A | 52.0% |
| Premix B | 22.0% |
| Non-ionic polymeric dispersing agent | 2% |
| Antimould agent | 0.1% |
| Silicon antifoam agent | 0.2% |
| Xanthan gum | 0.15% |
| Water | remainder to 100% |

The thus prepared formulation has the following characteristics:
a-cypermethrin titre 8%; total PBO titre 26%; density 1.04; pH 8-9; viscosity 200-800 cps; microcapsule dimension (average diameter): 5-10 micron; emulsion size 1-5 micron

Example 3

Preparation of a Formulation Based on Diazinon+PBO Microencapsulated in Polyurea (PU) and Microemulsified PBO Using the procedure shown in example 1, a formulation is prepared consisting of a PBO emulsion (8%) and of an aqueous suspension of diazinon+PBO encapsulated together (respectively 8% and 16%) in PU, starting from a premix A containing pure diazinon (10%) and PBO (20%) and from a premix B containing PBO (81%), with the following final composition:

| | |
|---|---|
| Premix A | 80.0% |
| Premix B | 9.9% |
| Non-ionic polymeric dispersing agent | 2% |
| Antimould agent | 0.1% |
| Silicon antifoam agent | 0.2% |
| Xanthan gum | 0.15% |
| Water | remainder to 100% |

The prepared formulation has the following characteristics
diazinon titre 7.9%; total PBO titre 24.1%; density 1.04; pH 8-9; viscosity 200-800 cps; microcapsule dimension (average diameter): 4-12 micron; emulsion size: 1-5 micron

Example 4

Preparation of a Formulation Based on Acetamiprid+PBO Microencapsulated in Polyurea (PU) and Microemulsified PBO Using the same method as described in example 1, a formulation is prepared consisting of a PBO emulsion (15%) and an aqueous suspension of acetamiprid+PBO microincapsulated together (5%) in PU, starting from a premix A containing acetamiprid (12%) and PBO (0.4%), and from a premix B containing PBO (81%) with the following final composition:

| | |
|---|---|
| Premix A | 42.0% |
| Premix B | 18.5% |
| Non-ionic polymeric dispersing agent | 2% |
| Antimould agent | 0.1% |
| Silicon antifoam agent | 0.2% |
| Xanthan gum | 0.15% |
| Water | remainder to 100% |

The prepared formulation has the following characteristics acetamiprid titre 4.9%; total PBO titre 15%; density 1.02; pH 8-9; viscosity 200-800 cps; microcapsule dimension (average diameter) 3-10 micron; emulsion size 1-5 micron.

Example 5

Preparation of a Formulation Based on Deltamethrin+PBO Microencapsulated in Polyurea (PU) and Microemulsified PBO Using the same method as described in example 1, a formulation is prepared consisting of a PBO emulsion (12%) and an aqueous suspension of deltamethrin+PBO encapsulated together (6 and 12% respectively) in PU, starting from a premix A containing deltamethrin (12%) and PBO (24%) and from a premix B containing PBO (81%) with the following final composition:

| | |
|---|---|
| Premix A | 50.0% |
| Premix B | 14.8% |
| Non-ionic polymeric dispersing agent | 2% |
| Antimould agent | 0.1% |
| Silicon antifoam agent | 0.2% |
| Xanthan gum | |
| Water | remainder to 100% |

The prepared formulation has the following characteristics:
deltamethrin titre 5.9%; total PBO titre 23.9%; density 1.06; pH 8-9; viscosity 200-800 cps; microcapsule dimension (average diameter) 5-14 micron; emulsion size 1-5 micron

Example 6

Preparation of a Formulation Based on Etofenprox+PBO Microencapsulated in Polyurea (PU) and Microemulsified PBO Using the same method as described in example 1, a formulation is prepared consisting of a PBO emulsion (20%) and an aqueous suspension of etofenprox+PBO encapsulated together (20%) in PU, starting from a premix A containing etofenprox (98%) and PBO (2.0%) and from a premix B containing PBO (81%), with the following final composition:

| | |
|---|---|
| Premix A | 21.0% |
| Premix B | 24.7% |
| Non-ionic polymeric dispersing agent | 2% |
| Antimould agent | 0.1% |
| Silicon antifoam agent | 0.2% |
| Xanthan gum | 0.15% |
| Water | remainder to 100% |

The prepared formulation has the following characteristics etofenprox titre 19.9%; total PBO titre 20.4%; density 1.01; pH 8-9; viscosity 200-800 cps; microcapsule dimension (average diameter) 5-10 micron; emulsion size 1-5 micron.

Example 7

Preparation of a Formulation Based on Z-Cypermethrin+PBO Microencapsulated in Polyurea (PU) and Microemulsified PBO Using the same procedure as in example 1 a formulation is prepared consisting of a PBO emulsion (15%) and an aqueous suspension of z-cypermethrin and PBO encapsulated together (both 10%) in PU, starting from a premix A containing z-cypermethrin (33%) and PBO (33%), and from a premix B containing PBO (81%), with the following final composition:

| | |
|---|---|
| Premix A | 33.0% |
| Premix B | |
| Non-ionic polymeric dispersing agent | 2% |
| Antimould agent | 0.1% |
| Silicon antifoam agent | 0.2% |
| Xanthan gum | 0.15% |
| Water | remainder to 100% |

The prepared formulation has the following characteristics z-cypermethrin titre 9.9%; total PBO titre 25.1%; density 1.02; pH 8-9; viscosity 200-800 cps; microcapsule dimension (average diameter) 6-14 micron; emulsion size 1-5 micron.

Example 8

Preparation of a Formulation Based on Fenazaquin+PBO Microencapsulated in Polyurea (PU) and Microemulsified PBO Using the same procedure as in example 1 a formulation is prepared consisting in a PBO emulsion (30%) and an aqueous suspension of fenazaquin+PBO encapsulated together (10%) in PU starting from a premix A containing fenazaquin al 25% e PBO al 1% and from a premix B containing PBO al 81% with the following final composition:

| | |
|---|---|
| Premix A | 40.0% |
| Premix B | 37.0% |
| Non-ionic polymeric dispersing agent | 2% |
| Antimould agent | 0.1% |
| Silicon antifoam agent | 0.2% |
| Xanthan gum | 0.15 |
| Water | remainder to 100% |

The prepared formulation has the following characteristics titolo fenazaquin 9.9%; total PBO titre 30.3%; density 1.02; pH 8-9; viscosity 200-800 cps microcapsule dimension (average diameter): 3-10 micron; emulsion size 1-5 micron

Example 9

Preparation of a Formulation Based on Pyridaben+PBO Microencapsulated in Polyurea (PU) and Microemulsified PBO Using the same procedure as in example 1 a formulation is prepared consisting of a PBO emulsion (20%) and an aqueous suspension of pyridaben+PBO microencapsulated together (5%) in PU, starting from a premix A containing pyridaben (16%) and PBO (3%), and from a premix B containing PBO (81%) with the following final composition:

| | |
|---|---|
| Premix A | 31.0% |
| Premix B | |
| Non-ionic polymeric dispersing agent | 2% |
| Antimould agent | 0.1% |
| Silicon antifoam agent | |
| Xanthan gum | 0.15 |
| Water | remainder to 100% |

The prepared formulation has the following characteristics:
pyridaben titre 4.9%; total PBO titre 20.8%; density 1.03; pH 8-9; viscosity 200-800 cps; microcapsule dimension (average diameter): 4-10 micron; emulsion size 1-5 micron.

Example 10

Preparation of a Formulation Based on Pyrimethanyl+PBO Microencapsulated in Polyurea (PU) and Microemulsified PBO Using the same procedure as in example 1 a formulation is prepared consisting of a PBO emulsion (20%) and an aqueous suspension of pyrimethanyl+PBO microincapsulated together (10%) in PU, starting from a premix A containing pyrimethanyl (33%) and PBO (3%), and from a premix B containing PBO (81%) with the following final composition:

| | |
|---|---|
| Premix A | 31.0% |
| Premix B | 24.7% |
| Non-ionic polymeric dispersing agent | 2% |
| Antimould agent | 0.1% |
| Silicon antifoam agent | 0.2% |
| Xanthan gum | 0.15 |
| Water | remainder to 100% |

The prepared formulation has the following characteristics:
pyrimethanyl titre 9.9%; total PBO titre 20.8%; density 1.03; pH 8-9; viscosity 200-800 cps; microcapsule dimension (average diameter): 4-12 micron; emulsion size: 1-5 micron.

Example 11

Preparation of a Formulation Based on Bifenthrin and PBO Microencapsulated in a Polyurea (PU) Multilayer System The preparation process is herein described of a formulation according to FIG. 1, where (A) is bifenthrin and (B) is PBO.

Using the method described in example 1, a bifenthrin-containing microcapsule concentrate is prepared starting from the following reagents:

| | |
|---|---|
| Pure bifenthrin | 20% |
| Solvent (Solvesso 200) | 20% |
| Voronate M220 | 2.87% |
| Hexamethylenediamine 40% | 2.75% |

-continued

| | |
|---|---|
| Lignin sulfonate | 1% |
| Soluble Ca and Na salts | 9% |
| Silicon antifoam agent | 0.2% |
| Xanthan gum | 0.1% |
| Water | remainder to 100% |

The microcapsule concentrate thus obtained is added to an organic solution containing PBO, polyisocyanate and the diammine under vigorous stirring in an aqeuos phase containing lignin sulfonate at a temperature of 50° C., as reported here below:

| | |
|---|---|
| Microcapsule bifenthrin (20%) | 10% |
| PBO 95% | 6.4% |
| Solvent (Solvesso 200) | 20% |
| Voronate M220 | 2.95% |
| Hexamethylendiammine 40% | 2.81% |
| Lignin sulfonate | 1% |
| Soluble Ca and Na salts | 9% |
| Silicon antifoam agent | 0.2% |
| Xanthan gum | 0.1% |
| Water | remainder to 100% |

The mixture is then maintained under stirring for 4 hrs at 50° C. Finally, the obtained microcapsule suspension is added with silicon antifoam agent, xanthan gum and soluble calcium and sodium salts, obtaining a suspension o multilayered microcapsules with viscosity 600-1200 cps.

Bifenthrin titre 1.98%; PBO titre 6.1%; density 1.07; pH 8-9; viscosity 600-1200 cps; microcapsule dimension (average diameter) 20-40 micron.

Example 12

Evaluation of Release Time from Polyurea Microcapsules at Room Temperature

The evaluation of release time for active principle and PBO from polyurea microcapsules is performed as follows:

The formulation containing active principle and PBO encapsulated together in PU and microemulsified PBO is diluted at a temperature of about 20° C. with distilled water, so as to obtain a dilution of agronomic type (e.g. 20 g active principle/1000 l water).

The suspension is homogenised under stirring, and a 100 ml sample thereof is withdrawn; the sample, maintained homogenised by stirring, is split into four 25 ml aliquots. Three aliquots are simultaneously transferred onto three glass plates, and kept at ambient conditions, respectively for 1, 2, 6 hrs.

At the end of each exposure time, the corresponding glass plate is washed with a fixed amount of n-hexane (which dissolves both active principle and PBO, but not the polymeric wall). The organic phase, containing all released active principle and PBO, is then analysed by HPLC, thereby assessing the amount of release at the given time point. The fourth aliquot, used to determine the release at time zero, is directly added with n-hexane; the organic phase, containing all PBO (and possible active ingredient) being immediately available form the formulation, is separated and assayed as above by HPLC, to determine the amounts of the two components.

The obtained release data are as follows:

Formulation of Example 1

| Time (h) | Microemulsified PBO (%) | Microencapsulated PBO (%) | bifenthin (%) |
|---|---|---|---|
| 0 | 100 | 0 | 0 |
| 1 | 100 | 95 | 20 |
| 2 | 100 | 100 | 65 |
| 6 | 100 | 100 | 100 |

Formulation of Example 2

| Time (h) | Microemulsified PBO (%) | Microencapsulated PBO (%) | a-cypermethrin (%) |
|---|---|---|---|
| 0 | 100 | 0 | 0 |
| 1 | 100 | 50 | 30 |
| 2 | 100 | 100 | 90 |
| 6 | 100 | 100 | 100 |

Example 13

Mortality Assay

The "leaf dip bioassay" used for testing the activity of insecticides against *Bemisia tabaci* (whitefly) biotype B, was similar to that described by Cahill, M et al, Bull. Entomol. Res. 85, 181-187, 1995.

Cotton plants (*Gossypium hirsutum* L.) were grown without any exposure to the insecticides. The leaves were cut up into disc shapes and immersed in an aqueous solution of insecticide containing 0.01% of Agral then left to dry at 25° C.

Control leaves were immersed in Agral and distilled water only.

About 20 adult insects were placed onto the small discs of treated cotton leaf.

The insects were allowed to feed and maximum mortality was evaluated at 24 and 48 hours.

By using the formulations prepared in example 1 the results given in table 1 were obtained.

LC50% a.i. (=active ingredient) and LC99% a.i. indicate the quantity of insecticide able to achieve mortality for 50% and 99% of the insects tested.

As a comparison, the data obtained with commercial bifenthrin in the absence of the synergistic compound (PBO) and the data obtained with commercial bifenthrin in a mixture with the same quantity of PBO present in the formulation product of example 1 are given in the same table.

The data demonstrate that the formulation of example 1 is much more effective.

TABLE 1

| PRODUCT | LC50% a.i. (ppm) | LC99% a.i. (ppm) |
|---|---|---|
| Bifenthrin | 0.01 | 257 |
| Bifenthrin + PBO mix. | 0.001 | 0.05 |
| Formulation ex. 1 | 0.000024 | 0.0003 |

The invention claimed is:

1. A formulation comprising:
   (a) a single layer microcapsule comprising:
      (i) a capsule wall comprising polyesters, polyamides, polyureas, polycarbamates, polyurethanes or urea-formaldehyde polymers;
      (ii) component (A) selected from the group consisting of Allethrin, Bioallethrin, Tetramethrin, Prallethrin, Cypermethrins, Esbiothrin, Permethrin, Fenpropathrin, Transfluthrin, Bifenthrin, Resmethrin, Bioresmethrin, Fenvalerate, Esfenvalerate, Etofenprox, Imiprothrin, Phenothrin, β-Cyfluthrin, Deltamethrin, Cyhalothrin, Imidacloprid, Acetamiprid, Thiacloprid, Thiodicarb, Carbosulfan, Carbofuran, Fenazaquin, Pyridaben, Fludioxonil, Imazalil, Pyrimethanil, Fenbendazole, Clotrimazole, Praziquantel, Fipronil, Pymetrozine and Pyridalyl, wherein (A) possesses insecticidal, acaricidal, fungicidal, snailcidal or vermicidal activity; and
      (iii) component (B) selected from the group consisting of piperonyl butoxide (PBO), sesamol, verbutin, MGK 264 and S,S,S-tributyl phosphorotrithioate (DEF), wherein (B) exhibits synergistic activity with (A) by enhancing its effectiveness; and
   (b) an immediate-release emulsion or microemulsion comprising an additional quantity of component (B),
   wherein the average release time of component (A) is delayed by a time of between 1 and 12 hours.

2. A formulation as claimed in claim 1, wherein the average release time of component (A) is delayed by a time of between 2 and 10 hours.

3. A formulation as claimed in claim 1, wherein the component (B) is PBO or verbutin.

4. A formulation as claimed in claim 1, wherein the material constituting the microcapsule wall represents a fraction of the capsule weight and varies between 5% and 30%.

5. A formulation as claimed in claim 1, wherein the average diameter of the microcapsule is between 1 and 100 micron.

6. A formulation as claimed in claim 1, wherein the average diameter of the microcapsule is less than 50 micron.

7. A formulation as claimed in claim 1 wherein the quantity of component (A) relative to component (B) in its total quantity is between 1% and 1500%.

8. A formulation as claimed in claim 7 wherein the quantity of component (A) relative to component (B) in its total quantity is between 2% and 200%.

9. A formulation as claimed in claim 7, wherein the quantity of component (A) relative to component (B) in its total quantity is between 5% and 100%.

10. A process for preparing the formulations described in claim 1, comprising the steps of:
    (i) preparing microcapsules comprising components (A) and (B); and
    (ii) dispersing the microcapsules obtained in (i) in an emulsion or a microemulsion of an additional quantity of component (B).

11. A process as claimed in claim 10 wherein in step (i) the microcapsule wall comprises polyurea and the microcapsules are formed by reacting in the presence of the material to be encapsulated:
    (a) a polyisocyanate, either alone or mixed with a variable quantity of another isocyanate, and
    (b) a polyamine,
    which gives rise to polyurea as a result of polymerization.

12. A process as claimed in claim 10 wherein in step (i) the microcapsule wall comprises polyamide and the microcapsules are formed by reacting in the presence of the material to be encapsulated:
    (a) an acid chloride either alone or mixed with a variable quantity of another acid chloride, and
    (b) a polyamine or a polyoxyalkylene polyamine alone or mixed with ammonia or with other amines or with inorganic bases to neutralize the acidity formed during polymerization.

13. A process as claimed in claim 10 wherein in step (i) the material constituting the microcapsule wall is polyester, polyurethane, polycarbamate or a urea-formaldehyde polymer.

14. A formulation obtainable by the process described in claim 10.

15. A Method for eradicating insects, mites, moulds, snails or worms comprising treating a substrate requiring treatment with a formulation or a composition described in claim 1.

16. A Method for eradicating insects, mites, moulds, snails or worms comprising treating a substrate requiring treatment with a formulation or a composition described in claim 14.

17. The process of claim 11, wherein said other isocyanate is toluene diisocyanate.

18. A process as claimed in claim 10 wherein in step (i) the material constituting the microcapsule wall is polyurea and the microcapsules are formed by reacting in the presence of the material to be encapsulated a polyisocyanate, either alone or mixed with a variable quantity of another isocyanate, through heating to induce a partial hydrolysis of the isocyanate groups which subsequently self-condense under hot conditions.

19. The process of claim 18, wherein said other isocyanate is toluene diisocyanate.

20. The process of claim 12, wherein said acid chloride is sebacoyl chloride.

* * * * *